United States Patent [19]
Jensen et al.

[11] Patent Number: 5,947,980
[45] Date of Patent: *Sep. 7, 1999

[54] DEVICE FOR SQUEEZING AND CUTTING AN UMBILICAL CORD

[75] Inventors: Knud Lykke Jensen, Kvistgård; Per Baunsgaard, Hedehusene, both of Denmark

[73] Assignee: Price Invena APS, Horsholm, Denmark

[*] Notice: This patent is subject to a terminal disclaimer.

[21] Appl. No.: 08/906,936

[22] Filed: Aug. 6, 1997

Related U.S. Application Data

[62] Division of application No. 08/618,357, filed as application No. PCT/DK94/00364, Sep. 30, 1994, Pat. No. 5,697,938.

[30] Foreign Application Priority Data

Sep. 30, 1993 [DK] Denmark .................. 1101/93

[51] Int. Cl.⁶ .......................... A61B 17/42; A61B 17/46
[52] U.S. Cl. .................. 606/120; 606/151; 30/272.1
[58] Field of Search ...................... 606/120, 158, 606/151, 174; 30/134, 90.6, 90.7, 162, 272.1, 124, 492, 250

[56] References Cited

U.S. PATENT DOCUMENTS

| | | | |
|---|---|---|---|
| 2,524,337 | 10/1950 | Whittaker | 606/120 |
| 3,631,858 | 1/1972 | Ersek | 606/174 |
| 3,774,251 | 11/1973 | Pellman | 30/134 |
| 4,428,374 | 1/1984 | Auburn | 606/120 |
| 4,557,049 | 12/1985 | Cribbs et al. | 30/124 |
| 4,716,886 | 1/1988 | Schulman et al. | 606/120 |
| 4,781,188 | 11/1988 | Collins | 606/120 |
| 4,831,734 | 5/1989 | De Ruyter et al. | 30/124 |
| 4,856,517 | 8/1989 | Collins et al. | 606/120 |
| 4,938,215 | 7/1990 | Schulman et al. | 606/120 |
| 5,014,431 | 5/1991 | Jebe et al. | 30/124 |
| 5,018,275 | 5/1991 | Huang | 30/124 |
| 5,462,555 | 10/1995 | Bolanos et al. | 606/120 |
| 5,509,205 | 4/1996 | Ragland, III | 30/162 |

FOREIGN PATENT DOCUMENTS

| | | | |
|---|---|---|---|
| 927085 | 5/1973 | Canada | 30/272.1 |

*Primary Examiner*—Richard J. Apley
*Assistant Examiner*—Justine R. Yu
*Attorney, Agent, or Firm*—Jacobson, Price, Holman & Stern, PLLC

[57] ABSTRACT

An improved disposable device for squeezing and cutting an umbilical cord comprising at least one clamp (1) having two legs interconnected by a hinge, said legs being supported in recesses of a holder (5). The holder further includes a knife (8). The umbilical cord is squeezed and cut when the holder is shifted along the clamp.

12 Claims, 4 Drawing Sheets

_5,947,980_

DEVICE FOR SQUEEZING AND CUTTING AN UMBILICAL CORD

This is a Division of application Ser. No. 08/618,357, filed Mar. 19, 1996, now U.S. Pat. No. 5,697,938, which is a continuation application on PCT/DK94/00364 designating the U.S., presently pending, entitled "A device for clamping and cutting e.g. an umbilical cord," and filed on Sep. 30, 1994 by the same inventors.

BACKGROUND OF THE INVENTION

1. Field of the Invention

The present invention relates to a device for squeezing and cutting an umbilical cord, and the device has at least one clamp with two legs interconnected by a hinge at one end of the clamp, and a holder by means of which the clamp can be closed. The holder has a knife cutting the umbilical cord after it has been squeezed by the clamp.

2. General Background

U.S. Pat. No. 4,856,517 relates to such a device where the holder consists of a lower part and an upper part interconnected by a hinge. The holder has two grooves into which two open clamps can be inserted. When the holder closes on an umbilical cord, the clamps are also closed. The holder and the clamps are locked in the end position. After the umbilical cord has thus been squeezed in two places, it is cut by a slide and knife being shifted on the holder between the two clamps. The locking mechanism of the holder is then released, and the two squeezed parts of the umbilical cord can be released from the holder.

Because of the two-piece holder and the separate slide this prior art device is very complicated to make. And when the holder is opened after an umbilical cord has been cut, the knife is exposed which has to be considered very unfortunate from a safety point of view.

SUMMARY OF THE PRESENT INVENTION

The objective of the invention is to provide an improved device of the said kind but without the above-mentioned disadvantages. The device of the present invention is simpler to make (fewer parts and simpler shapes), and the knife is placed so that it is always inaccessible. According to the Danish Working Environment Service, inaccessibility means that no access to the knife has an opening larger than approx. 6 mm.

According to the invention this is achieved by the holder being provided with a through-going bore of a design allowing the hinged end of the clamp to be inserted in the bore and of a size allowing the holder to be moved along the legs of the clamp so that the clamp is closed and the knife of the holder is stationary and placed in such a way that the umbilical cord is cut when the clamp is closed and the holder is shifted further along the legs of the clamp.

To cut an umbilical cord, two clamps are normally used, and according to the invention it is, therefore, expedient that the holder should have a second identical bore, in parallel with the first-mentioned bore, for a second identical clamp and that the knife should be placed between the two bores.

In the said device, the knife is stationary inside the holder so that it will not be accessible even after cutting an umbilical cord. And the holder is constituted e.g. by a die cast part without a separate slide. The entire device thus consists of a holder and one or two clamps.

According to the invention it is expedient that the second clamp should have a catch at the free end of the legs for locking the clamp in the closed position, and that the second bore should open outwards and be equipped with blocking devices which interact with corresponding devices on the second clamp in order that the second clamp can be withdrawn through the opening when the holder is shifted past the position in which the clamp is locked and the umbilical cord is cut. When the umbilical cord has been cut, the second locked clamp can then be separated easily from the holder which is still locking the first clamp.

DETAILED DESCRIPTION OF THE PREFERRED EMBODIMENT

Figure 1:
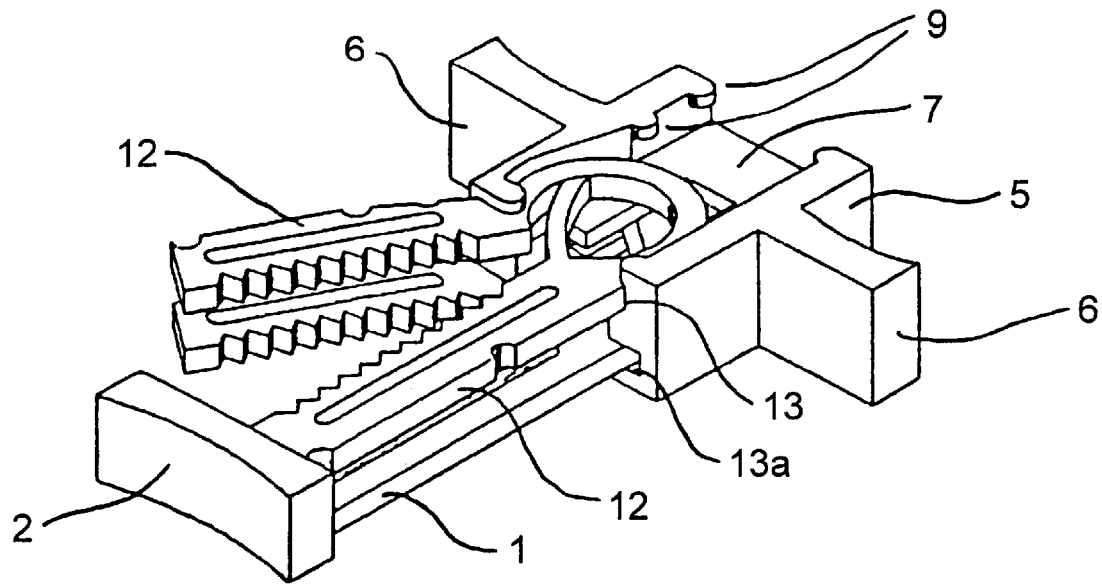
FIG. 1 is a perspective of the disposable safety squeezing device in the open position, with two clamps of which the control clamp faces downward, FIG. 2 a side view of the disposable squeezing device in the open position and with the control clamp mounted FIG. 3 a side view of the holder seen from one side, FIG. 4 a side view of the control clamp in the open position, FIG. 5 a side view of the second clamp in the open position, FIG. 6 a side view of the holder seen from a bottom side, and FIG. 7 a perspective of the disposable safety squeezing device in the closed position, with one clamp released after the umbilical cord has been cut.
Figure 2:
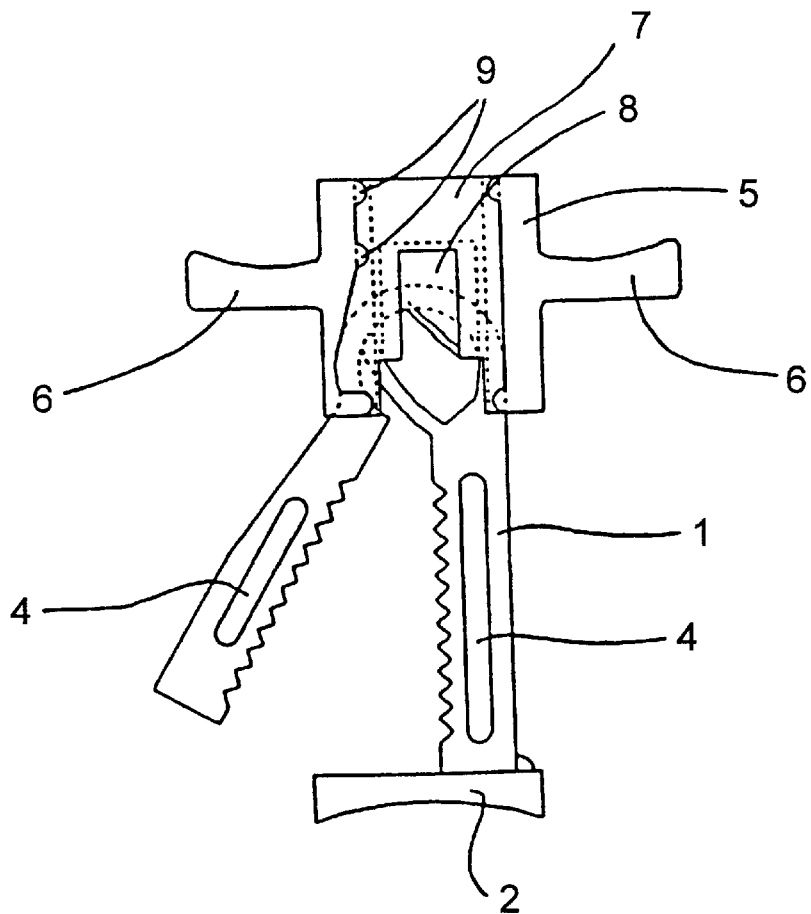
Figure 3:
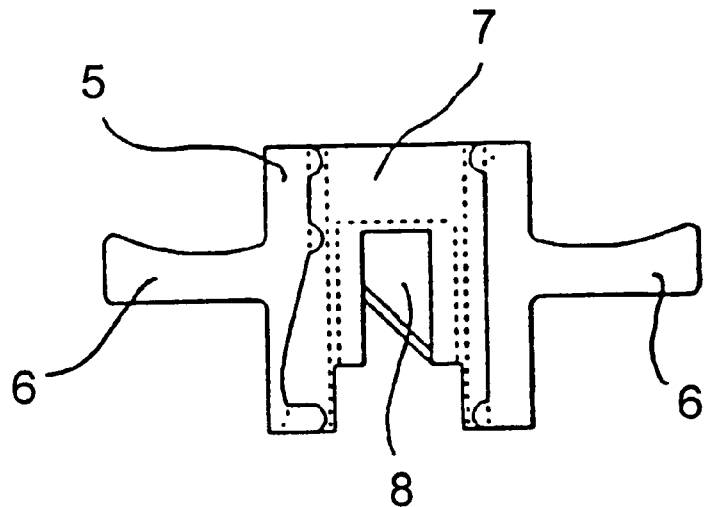

FIG. 1 shows a disposable double squeezing device with a control clamp 1 and a second clamp 12.

The hinge ends of the control clamp 1 and the second clamp 12 are pushed into through-going bores or grooves 13 and 13*a* in the holder 5.

The holder 5 has two control tabs 6 and a partition 7 between the two grooves 13 and 13*a*. An inclined knife 8 is mounted in the partition 7.

Clamps 1 and 12 are secured in one direction in grooves 13 and 13*a* of the holder by their initial tension. In the opposite direction, at right angles to the first-mentioned direction, the control clamp 1 is secured by the outer wall 14 which closes the groove 13*a*, and some projections 9 which close the groove 13 for the second clamp 12.

Figure 4:
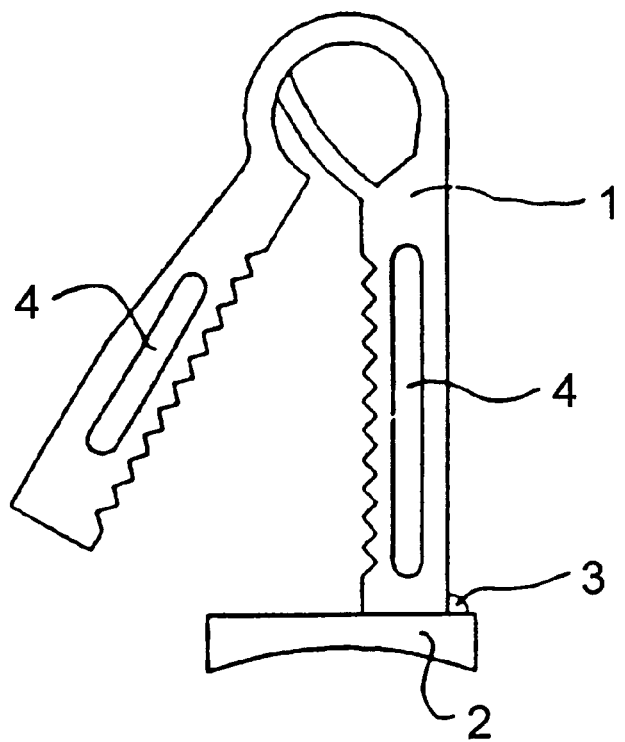
Figure 5:
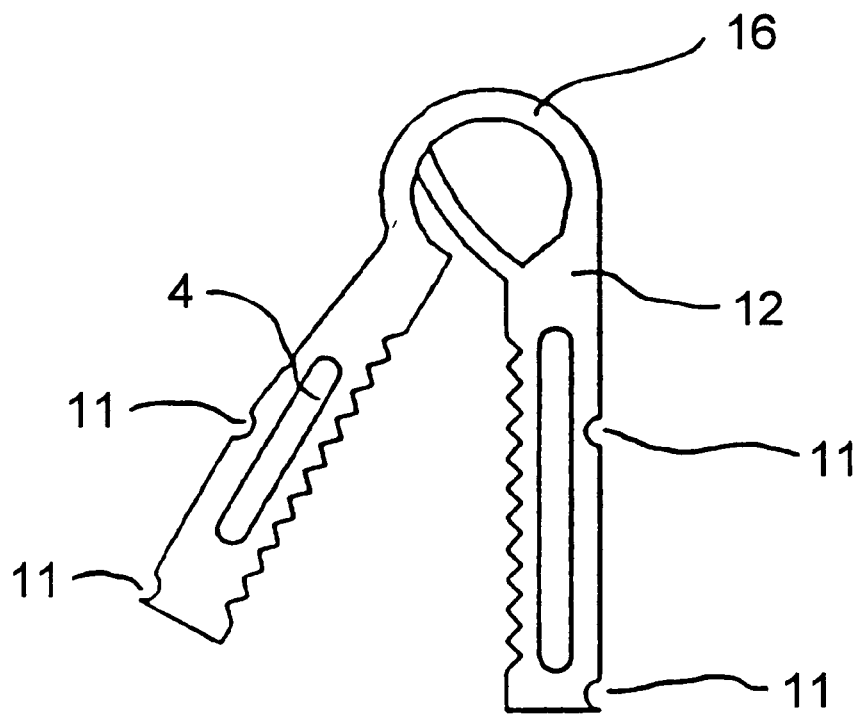
Figure 6:
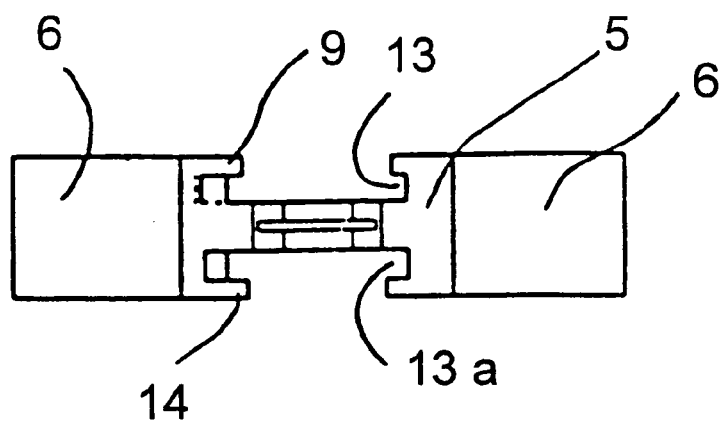

The control clamp 1 has a contact part 3 (FIG. 4) which, when it is desired to use the second clamp 12, secures the latter in the same fixed position as the control clamp 1.

The second clamp 12 has recesses 11 which after shifting of the holder 5 to the closed position (FIG. 7) are placed opposite to the projections 9 on the holder. In this position it is possible to release the second clamp 12 from the holder 5.

In its closed position the second clamp 12 is locked to the object by the catch 15.

Both clamps have recesses 4 in their longitudinal direction which secure that deformations caused by squeezing will take place in these recesses.

The umbilical cord is inserted in the opening between clamps 1 and 12 (FIG. 1).

The control clamp 1 has a control part 2 which is used as a counter pressure part when the holder 5 is shifted with two fingers on the control tabs 6.

Figure 7:
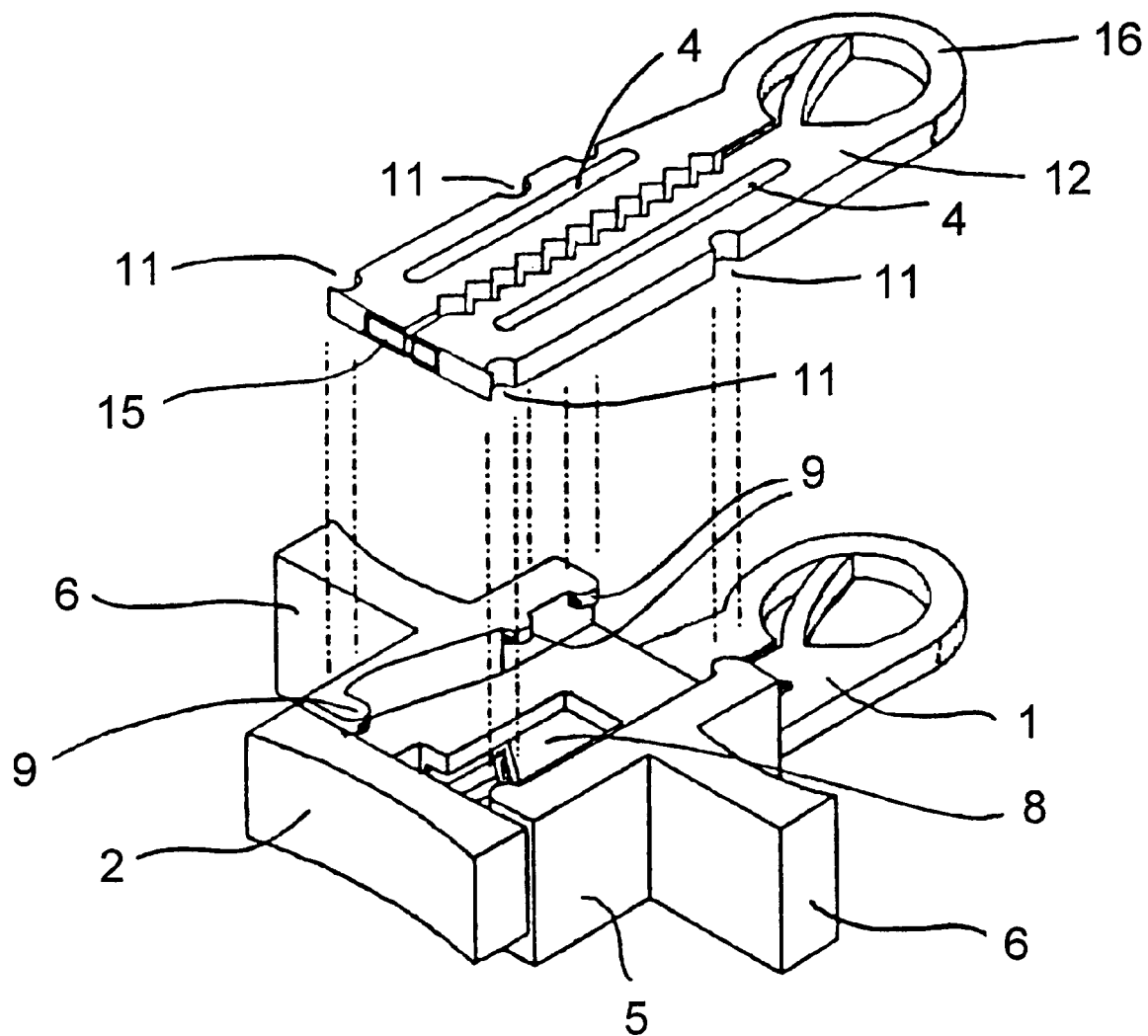

The umbilical cord is squeezed during the first stage of shifting. Further shifting brings the inclined knife 8 of the holder into contact with the umbilical cord which is then cut (FIG. 7). After cutting, the control clamp 1 continues to squeeze one part of the umbilical cord. For releasing this part of the umbilical cord, the holder 5 just has to be shifted in the opposite direction.

When released from the holder 5, the second clamp 12 remains locked in the closed position by the catch 15 and is released by cutting the spring bow 16 of the clamp.

What is claimed as an invention is:

1. A device for squeezing and cutting a member, which device comprises:

a clamp having a pair of legs hinged together at a hinge at one end and openable apart to form an opening to receive a member between said pair of legs for squeezing and cutting the member;

a clamp holder mounted in sliding relationship with said clamp, engaging each of said legs of said clamp such that when the clamp holder is slid along said clamp from said one hinged end toward the other end of the pair of legs, said legs are thereby forced together by said clamp holder; and cutting means carried by said clamp holder and positioned to pass alongside said opening between said pair of legs of said clamp so as to cut said member when present in said opening when said clamp holder is slid along said clamp.

2. A device as claimed in claim 1, wherein said clamp is provided with an abutment member distal from said hinge against which manual pressure is applied to slide the clamp with respect to the clamp holder.

3. A device as claimed in claim 1, wherein the clamp holder has a pair of oppositely directed finger engageable projections by which finger pressure is applied to slide the clamp holder along the clamp.

4. A device as claimed in claim 1, further comprising a second clamp having a pair of legs hinged together at one end and openable apart to form an opening to receive said member between said legs for squeezing and cutting; wherein:

said clamp holder being mounted in sliding relationship with said second clamp such that said first and second clamps are positioned in a spaced apart mutually overlying relationship, such that said clamp holder engages each of said pairs of legs of each said clamp and the clamp holder is slid along said clamps in a sliding movement from said one end toward the other end of the pair of legs so as to force the pairs of legs of each clamp together, and said cutting means being positioned on said clamp holder so as to pass between said mutually overlying clamps during said sliding movement of the clamp holder so as to cut said member held between said clamps when present in said openings when the clamp holder is slid along said clamps.

5. A device as claimed in claim 4, wherein said clamp holder is mounted in sliding relationship with said second clamp to permit removal of the second clamp from said clamp holder after completion of said sliding movement of the clamp holder.

6. A device as claimed in claim 4, wherein said second clamp is removed in a direction transverse to said sliding movement.

7. device as claimed in claim 4, wherein said clamp holder comprises a pair of opposed wall members connected by a web member carrying said cutting means, said clamps being received between said wall members and being compressed therebetween during said sliding movement.

8. A device as claimed in claim 7, wherein said wall members have on each side of said web member projections directed into a gap between the wall members and spaced from said web member to define channels in each of which channels a respective said clamp slides.

9. A devices as claimed in claim 8, wherein the channels in which slides the second clamp are defined between said web member and longitudinally spaced projections from said wall members and said second clamp has recesses therein which align and match with said projections when the clamp is in a release position following sliding of the clamp member therealong; whereby following squeezing and cutting of said member said second clamp is removed from the clamp holder transversely with respect to a direction of said sliding movement of said clamp holder by passage of said projections through said recesses.

10. A device as claimed in claim 7, wherein said cutting means is set back from a front in a direction of movement of the sliding movement of said clamp holder between the opposed wall members and is thereby shielded from accidental injury of the user.

11. A device as claimed in claim 4, wherein said second clamp has a catch located distally from said hinge for holding the legs of said clamp together once the legs have been squeezed together by said clamp holder.

12. A method for squeezing and cutting a member comprising positioning said member to extend through a squeezing and cutting device, which device comprises:

a clamp having a pair of legs hinged together at one end and openable apart to form an opening to receive said member between the legs for squeezing and cutting;

a clamp holder mounted in sliding relationship with said clamp, engaging each of said legs of said clamp such that the clamp holder is slid along said clamp from said one end toward the other end of the legs of the clamp so that said legs are thereby forced together by said clamp holder; and cutting means carried by said clamp holder and positioned to pass alongside said opening between said legs of said clamp in a sliding movement;

sliding said clamp holder along said clamp to close the legs of said clamp to squeeze said member, and cutting said member by the operation of said cutting means.

* * * * *